US007835076B2

(12) United States Patent
Roorda et al.

(10) Patent No.: US 7,835,076 B2
(45) Date of Patent: Nov. 16, 2010

(54) OPTICAL SYSTEM FOR ILLUMINATION OF AN EVANESCENT FIELD

(75) Inventors: Robert Roorda, Oxfordshire (GB); Derek Toomre, New Haven, CT (US)

(73) Assignee: Yale University, New Haven, CT (US)

( * ) Notice: Subject to any disclaimer, the term of this patent is extended or adjusted under 35 U.S.C. 154(b) by 222 days.

(21) Appl. No.: 12/083,711

(22) PCT Filed: Oct. 26, 2006

(86) PCT No.: PCT/US2006/041764

§ 371 (c)(1),
(2), (4) Date: Sep. 15, 2008

(87) PCT Pub. No.: WO2007/050743

PCT Pub. Date: May 3, 2007

(65) Prior Publication Data

US 2009/0168159 A1    Jul. 2, 2009

(51) Int. Cl.
*G02B 21/06* (2006.01)
*F21V 13/12* (2006.01)

(52) U.S. Cl. .................................................... 359/387
(58) Field of Classification Search ................ 359/385, 359/387; 362/268, 277
See application file for complete search history.

(56) References Cited

U.S. PATENT DOCUMENTS

| 4,498,742 | A * | 2/1985 | Uehara ........................ 359/385 |
| 5,675,401 | A | 10/1997 | Wangler et al. |
| 5,808,759 | A * | 9/1998 | Okamori et al. ................ 359/15 |
| 6,243,206 | B1 * | 6/2001 | Wangler ....................... 359/621 |
| 6,897,942 | B2 * | 5/2005 | Shiraishi ....................... 355/67 |
| 6,992,820 | B2 | 1/2006 | Abe et al. |
| 7,042,638 | B2 | 5/2006 | Gonschor et al. |
| 2003/0156269 | A1 | 8/2003 | Komatsuda |
| 2004/0240046 | A1 * | 12/2004 | Tischer et al. ................ 359/361 |
| 2004/0246573 | A1 * | 12/2004 | Tsuchiya et al. ............. 359/385 |
| 2004/0257669 | A1 | 12/2004 | Koehler |
| 2004/0263821 | A1 | 12/2004 | Oskotsky et al. |
| 2006/0126063 | A1 | 6/2006 | Cluzel et al. |

(Continued)

FOREIGN PATENT DOCUMENTS

EP    1211561    6/2002

OTHER PUBLICATIONS

McLeod, John H., *The Axicon: A New Type of Optical Element*, Journal of the Optical Society of America, Aug. 1954, vol. 44, No. 8 (pp. 592-597).

(Continued)

*Primary Examiner*—Mark Consilvio
(74) *Attorney, Agent, or Firm*—Ohlandt, Greeley, Ruggiero & Perle, L.L.P.

(57) ABSTRACT

A system of optics used to provide illumination through an objective at a precise inclination angle and with uniform intensity across an illuminated field. The system provides annular illumination with a continuously variable diameter at the back aperture of an objective. The resultant illumination field at the imaging plane of the objective includes rays with a single inclination angle with respect to the optical axis of the objective. This incidence angle is determined by the position of an axicon lens. The imaging plane is illuminated from 360 degrees rotation about optical axis of the objective.

27 Claims, 1 Drawing Sheet

U.S. PATENT DOCUMENTS

2007/0014002 A1    1/2007    Vodyanoy et al.

OTHER PUBLICATIONS

Stout, Andrea L., et al., *Evanescent Field Excitation of Florescence by Epi-illumination Microscopy*, Applied Optics, Dec. 1989, vol. 28, No. 24 (pp. 5237-5242).

International Search Report dated May 4, 2007 for PCT International Application No. PCT/US2006/041764.

Written Opinion dated May 4, 2007 for PCT International Application No. PCT/US2006/041764.

* cited by examiner

OPTICAL SYSTEM FOR ILLUMINATION OF AN EVANESCENT FIELD

BACKGROUND OF THE INVENTION

1. Field of the Invention

The present disclosure relates to microscopy, specifically to an illuminating optical system that illuminates a sample using total internal reflection. The invention may have broader uses including illumination for lithographic applications.

2. Description of Related Art

Fluorescent microscopy is a key tool in nearly all basic science labs and core facilities. Since the advent of genetically encoded tags, such as green fluorescent protein (GFP) and it's rainbow of color variants there has been an explosion in the use of fluorescent live cell imaging to major basic cellular processes. The easiest type of illumination is epi-fluorescent microscopy which typically uses a mercury arc lamp for Koehler illumination. Although this is the most popular fluorescent illumination method in terms of easy of use, it has the disadvantage that the whole cell is illuminated and the axial resolution is poor. To address the need for improved axial resolution and 'optical sectioning' the commercial confocal microscope was developed; common confocals are laser scanning or disk scanning. These instruments have an axial resolution of approximately 500 nm and are in wide use in the biological and material sciences. Its limitations are the requirement for lasers and specialized hardware and software and relatively poor sensitivity. Another form of light microscopy that provides thinner optical sectioning and much greater sensitivity is Total Internal Reflection Fluorescent Microscopy (TIRF; also called evanescent wave microscopy), as discussed below.

TIRF employs a totally internally reflected light (usually from a laser) to selectively illuminate and excite fluorophores in a very thin region (approximately 20-200+ nm) immediately adjacent to a glass-water (or glass-cell) interface. The evanescent field which 'tunnels' into the higher refractive index medium (e.g. aqueous or cell cytosol) exponentially drops in intensity along the z-axis and fluorophores away from the surface are not excited; the penetration depth depends on the wavelength, refractive indexes of the two mediums and the angle of the incident light. This optical method yields high signal-to-noise (S/N) images that is unmatched by any other light microscopy technique. It has greatly facilitated visualization of numerous cell surface process, such as signaling, exocytosis, endocytosis, migration, cytoskeleton, etc. The S/N is so high that single molecules can be directly studied, allowing biochemistry studies at the single molecule level in vivo and in vitro.

Penetration depth can be calculated by the below formulas:

Snell's law:

$$n_1 \sin\theta_1 = n_2 \sin\theta_2$$
$\theta$ = angle of incidence, n = refractive index Critical angle:

At the critical angle, $\theta_c$, $\theta_2 = 90°$; $\sin 90° = 1$;
$$n_1 \sin\theta_c = n_2$$
$$\theta_c = \sin^{-1}(n_2/n_1)$$

If $n_1 = 1.515$ and $n_2 = 1.36$, $\theta_c = \sin^{-1}\left(\frac{1.36}{1.515}\right) = 63.85°$ Evanescent field:

$$I_z = I_0 \exp^{-z/d_p}$$

$$d_p = \frac{\lambda}{4\pi\sqrt{n_1^2 \sin^2\theta_1 - n_2^2}}$$

I = intensity, z = distance, $\lambda$ = wavelength,
$d_p$ = penetration depth

For TIR: n1>n2 (n=refractive index of medium1 and medium2; n1 is usually glass and n2 is usually aqueous). One can only use the formula for the evanescent field (3rd box), or to be more complete all 3 boxes can be used, wherein for TIR to occur the critical angle (defined above) must be exceeded.

With this technique, specimens (usually cells or tissue) are generally plated on glass coverslips and illuminated from the glass side with light that is incident at an angle greater than the so called 'critical angle' for transmission of light through the glass/cell cytosol interface. A prerequisite for TIRF is that the refractive index of the second medium (e.g. the cell cytosol (R.I. approximately 1.36-1.38) or water (R.I. approximately 1.33)) is less than the refractive index of the coverslip; the latter is typically 1.51 for standard coverslip glass, but other higher refractive index material such as sapphire may (R.I. approximately 1.78) be employed such as sapphire. Under these conditions a very shallow evanescent light field is generated that penetrates from the interface into the specimen. This is often termed "evanescent illumination". The depth penetration of the illumination beyond the glass depends strongly on the incidence angle of the illumination light with respect to the glass surface.

One general class of instrumentation for TIRF imaging is "objective-type TIRF". In this arrangement a single microscope objective lens is used for both evanescent illumination and also for recording images of fluorescent features. This technique is simple and cheap compared to alternative methods and has the advantage of allowing easy access to the side of the imaged specimen that is facing away from the objective lens.

A basic requirement of this method is that the numerical aperture of the objective lens is higher than the refractive index of the aqueous medium where total internal reflection occurs (typically water or cell cytosol), thus practically the numerical aperture (N.A.)>1.38 to achieve TIRF in cells (and generally the higher the better). Only in the last decade have the major microscopy manufactures been able to produce high N.A. lens (N.A. 1.45-1.65) so as to easily achieve TIRF with cells using 'objective-type' illumination. With sufficiently high N.A. objective lenses evanescent illumination can be generated from light passing near its extreme angular acceptance limit (in the back focal plane). Specifically, this corresponds to light passing through an annular band near the outer edges of objective entrance pupil. Light passing inside this 'critical' diameter has a sub-critical incidence angle at the interface of glass and specimen and is transmitted through the interface as regular, deep illumination. Light passing outside this 'critical' diameter can generate an evanescent illumination field.

This method of objective-TIRF illumination was first described in the following article: Stout, Al, Exelrod, D., "Evanescent Field Excitation of Fluorescence by EPI-Illumination Microscopy", Applied Optics, 28 (24): 5237-5242, Dec. 15, 1989. This article describes four optical systems for evanescent illumination. In all of these arrangements an annular aperture is used to create an annular illumination pattern. This mask is located outside a conventional inverted fluorescence microscope and the pattern is relayed to the back pupil of the objective with lenses. A laser or an arc-lamp is indicated as the light source. The annular mask has a fixed position and a fixed diameter.

It should be noted that in one of the optical systems presented a conical axicon lens is used to improve light collection from an arc lamp source. This is the first mention of an axicon with regard to a TIRF imaging system. The axicon has a fixed light incidence angle.

TIRF is over twenty (20) years old and like the first confocal microscopes all setups were custom built, usually using a prism to couple the light into the sample. Again, only recently have microscopy companies developed high refractive index objective lens (1.45-1.65 N.A.) that permit one to do "objective-type" TIRF with cells. The latter has the advantage over "prism-type TIRF" that full access to the sample is permitted and could readily be adapted with these new lens. Objective-type TIRF also is more effective in collecting near-field emitted light than prism-type setups which typically use a water-immersion objective and collect far-field light that is transmitted through the aqueous medium.

TIRF have been extremely popular with scientists as they offer unmatched high-resolution imaging of processes near the cell surface. Analogous to confocal microscopes (including 2-photon microscopes) manufacturers have launched a whole series of instruments for this market (which are largely objective-type). Currently most objective-type TIRF instruments share a common design whereby laser light is focused onto a spot on the outer periphery of the back focal plane of the high NA objective lens. Although effective, major disadvantages have resulted from this approach: (1) the laser light easily generates interference effects, (2) the illumination is non-uniform and varies in penetration depth across the sample, (3) alignment of the system by the user is tricky as the spot can be placed in multiple equivalent positions, and (4) at deeper penetrations there is often a pronounced sideways scattering by the sample (due to illumination from the side and refractive index mismatch) which yields images that are smeared in a 'coma'-type manner.

An alternative approach involves using a ring of light to illuminate the back focal plane. This has been achieved using a mask with an annular aperture to block the central portion of a Gaussian beam. While simple to implement the majority of the light is lost, requiring the use of a powerful laser. Second, the use of a wide enough annulus (e.g., 200 microns) to collect adequate light makes it hard to create a thin evanescent field, and thus the penetration depth is deeper than desired. Third, in order to change the angle of illumination requires insertion of a new mask with a different diameter annulus and recalibration. In application, this approach is neither efficient nor practical.

Another option would be to scan the back focal plane of a disk in a radial manner. This can remove in-homogeneities and decrease scattering, but either requires a spinning wedge or scanning of the back focal plane using galvomirrors or equivalent devices.

U.S. Pat. No. 6,992,820 describes a method of coupling the output of a laser, using an optical fiber, through a microscope, to the back pupil plane of an objective for the purpose of TIRF microscopy. The position of the relayed image of the optical fiber in the back pupil plane can be adjusted by moving the fiber tip. With this adjustment a range of incidence angles can be realized.

U.S. Pat. No. 7,042,638 is only slightly different than U.S. Pat. No. 6,992,820. The primary differences lie in the route by which light is routed into the microscope. Light from a fiber optic is routed to a single point in the back pupil plane of an objective.

Axicon optics were first introduced in the following paper. McLeod, J H, "The Axicon—A New Type of Optical Element, Journal of Optical Society AM, 44 (8): 592-597, 1954. McLeod coins the term "axicon" in this paper. It is defined broadly as: "all axicons are figures of revolution. An axicon has the property that a point source on its axis of revolution is imaged to a range of points along its axis." Although conical lens are axicons the term axicon does not explicitly refer to conical lenses.

European Patent EP1211561A2 describes an illumination system for lithography that uses two axicons placed near a focal point in a scanned beam. The axicon spacing is adjustable and is used to control the coherence of light illuminating the field of an objective lens. A stationary integrating rod placed at a image plane is used to homogenize the light to achieve uniform illumination.

U.S. Pat. No. 5,675,401 describes an illumination system for lithography that uses two axicons placed inside a zoom lens, at a location where the beam through the axicon could either be converging or diverging depending on the zoom setting of the lens. The axicon spacing is adjustable and is used to control the coherence of light illuminating the field of an objective lens.

The present disclosure overcomes the disadvantages in conventional fixed axicon illumination system by providing an illumination system which uniquely provides: (1) a routine adjustment for incidence angle that is easily automated; (2) a small circular mask resulting in an insignificant light loss compared to a much larger loss from the annular aperture presented; and (3) elimination of the effects of laser speckle and interference fringes.

The present disclosure overcomes the disadvantages with regard to U.S. Pat. No. 6,992,820 by providing an illumination system which illuminates from 360 degrees around the optical axis of the objective lens. This reduces undesirable shadowing artifacts that can be caused by features in specimens. In addition, the present disclosure uniquely creates a uniform illumination field and eliminates speckle by temporally varying the illumination field.

The present disclosure relates to a novel system of total internal reflection fluorescent optics that is superior to conventional systems. The present disclosure offers better image quality, improved optical efficiency, and a unique depth penetration adjustment.

In addition, the present disclosure exhibits the following advantages over conventions system:

Improved uniformity of illumination
Reduced interference
Reduced 'coma' effect
Reduced shadowing from objects blocking illumination
Easy control of penetration depth
Ease of use and alignment
Designed for use with all objectives
Cost-effective Because the optics of the present disclosure illuminates a continuous 360 degree ring in the pupil of a TIRF objective, the illumination is extremely uniform. The shadowing problem inherent to illumination systems that have sources on only one side of the field of view is greatly reduced. It also reduces interference fringe effects. This results in much more homogeneous illumination and allows for better quantitative measurements to be made from TIRE images.

Additionally, the present disclosure allows for the radius of the illumination to be rapidly adjusted by adjusting the distance of the axicon from the focal point. This directly adjusts the illumination angle and the penetration depth of the evanescent field created. With this control a user has the ability to easily probe to different depths.

SUMMARY OF THE INVENTION

An illumination system for shaping a light beam, said system comprising: a light source; an optical assembly; an adjustable axicon lens; an image plane; a diffuser disposed adjacent to a surface of said image plane, wherein said image plane is disposed between said adjustable axicon lens and said diffuser; and a pupil plane. Further, the system may include an illumination field lens disposed between said diffuser and said pupil plane.

Preferably, the light source is at least one selected from the group consisting of: an optical fiber and a laser, e.g., a visible laser.

The optical assembly comprises at least one optical element selected from the group consisting of: a lens, a mask and a stationary axicon lens. Preferably, the optical assembly comprises a first lens, a stationary axicon lens, a mask and a second lens. Optionally, the first lens is disposed between said light source and said stationary axicon lens, said mask is disposed between said stationary axicon lens and said second lens, and said second lens is disposed between said mask and said adjustable axicon lens.

The position of said adjustable axicon lens is adjustable with respect to said image plane. The adjustable axicon lens is adjustable either manually or automatically.

The optical assembly converges said light beam from said light source, thereby forming an annular image, and the position of said adjustable axicon lens controls a radius of said annular image; wherein said annular image is focused on said image plane.

The present disclosure also pertains to a method for shaping a light beam comprising: emitting said light beam from a light source; passing said light beam through an optical assembly wherein said light beam is converged to form an annular image; adjusting the radius of said annular image; focusing said annular image on an image plane; diffusing the light of said annular image from said image plane; and creating uniform illumination on a pupil plane. This method may further comprise collimating light from said image plane and centering said collimated light on said pupil plane.

A further embodiment of the present disclosure is a microscopy assembly comprising: a light microscopy; and an illumination system for shaping a light beam, said system comprising: a light source; an optical assembly; an adjustable axicon lens; an image plane; a diffuser disposed adjacent to a surface of said image plane, wherein said image plane is disposed between said adjustable axicon lens and said diffuser; and a pupil plane. Preferably, the light microscopy is total internal reflection fluorescent microscopy.

The present disclosure can be used in the following applications, e.g., near field fluorescence imaging of cells and tissue, near field photo-activation and of cells and tissue, near field photo-bleaching of cells and tissue, in-vitro assays, screens, surface plasmon resonance and single molecule imaging. It can work on both live and fixed specimens. It can also be combined with other imaging modalities including, but not limited to, FRET, FLIP, confocal, brightfield, and epi-fluorescence.

DETAILED DESCRIPTION OF THE PREFERRED EMBODIMENT

Figure 1:
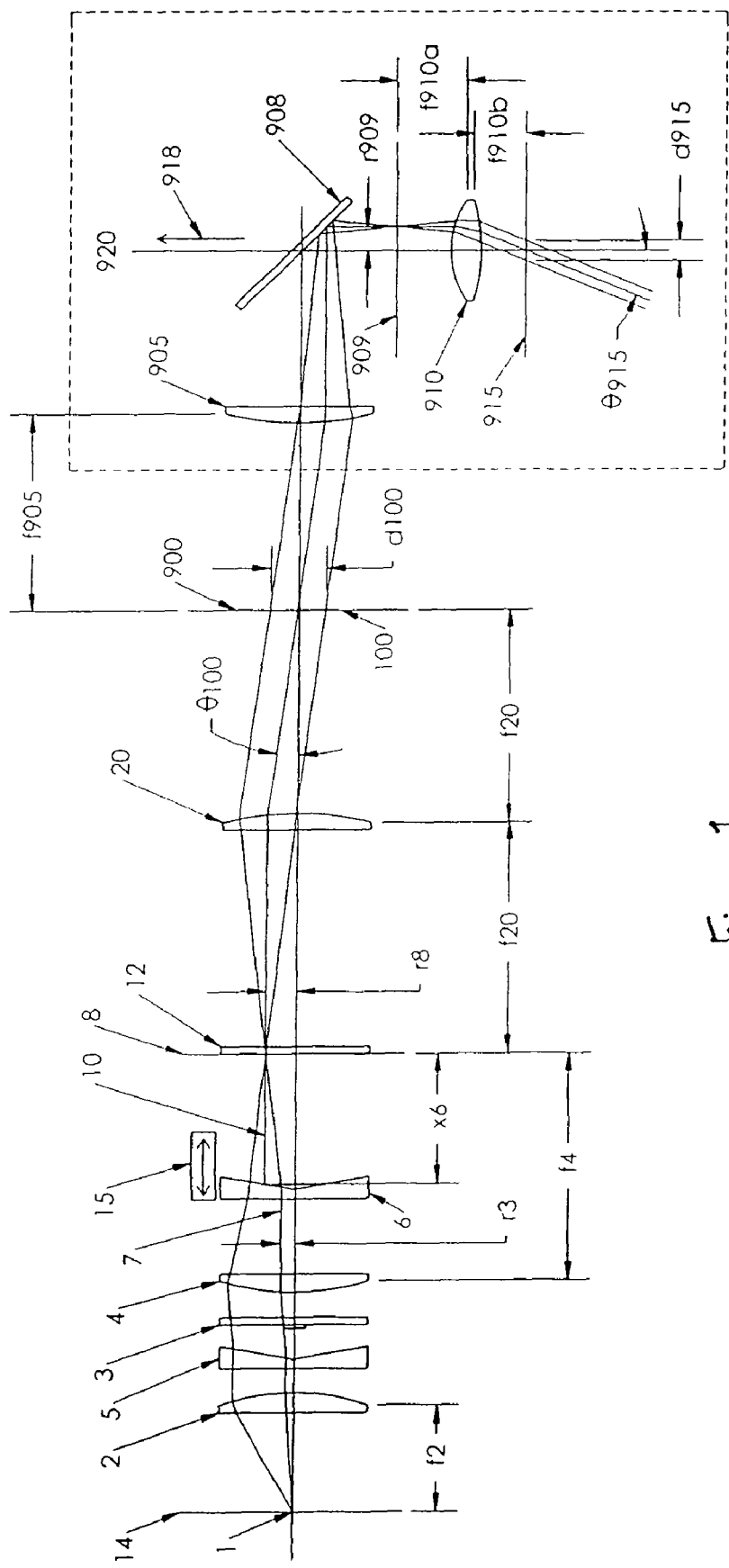
FIG. 1 is an illustration of an optical system used to illuminate the field of a microscope in accordance with the present disclosure.

An illumination system for total internal reflection fluorescence (TIRF) microscopy. The improved system includes an adjustment feature that allows the angle of incidence of illumination light to be set. The optical layout is designed to insure illumination intensity is constant through its range of adjustment to allow quantitative comparisons between recorded images. It illuminates about the full 360 degrees of azimuth angle of a microscope objective. It has uniform intensity across a field of view. It is temporally 'averaged' to eliminate the effects of laser speckle. The invention was conceived as an 'add-on' to be used with a microscope. It could, however be utilized as in integrated piece of a larger optical system.

Additionally, the present disclosure uses the axicon spacing to determine the inclination angle of the illumination. In addition, the present disclosure masks off the center of the beam to eliminate light from imprecise portions of the axicon. Also unique to the present disclosure is the use of a moving diffuser placed in a pupil plane to spatially spread out the illumination and to temporally vary it so as to eliminate speckle and create a uniform illumination field.

The present disclosure includes a conical lens (a conical axicon lens) placed in either a converging or a diverging beam. In the preferred embodiment it is placed in a converging beam to produce a real image that is an annular illumination pattern. By moving the conical lens along the optical axis of the system the diameter of the illuminated annulus can be varied. The annular image remains in focus though the complete adjustment range.

The annular illumination pattern is relayed to the back entrance pupil of a TIRF microscope objective where it is centered on the optical axis. This is usually best accomplished with a telecentric telescope. If the relay optics are telecentric the illumination remains Köhler through the entire range of the adjustment. Within the entrance pupil of the objective the radius of the annular illumination corresponds to the incidence angle of the light illuminating the image plane.

The present disclosure also includes a thin diffuser that is placed at the image plane of the annular illumination. The scattered light is projected forward from all points on the annulus as cones of light diverging in both the radial and tangential directions. This divergence results in light from every point along the annulus illuminating all locations in the image plane of the objective. The illumination is further homogenized by moving the diffuser within the plane of the annular image. This temporally scrambles the illumination. The diffuser motion must be sufficiently rapid that variations in the illumination are averaged out in the time an image is recorded. This can be readily accomplished by using a circular diffuser mounted on a fast motor. Holographic diffusers are particularly well suited for this application. They have a very thin diffusing surface and can be designed to diffuse light randomly over a specific angular range when light is incident at near-normal incidence angles. They also have a very high optical throughput compared to traditional diffusers such as an etched glass surface.

The present disclosure is useful for many applications that require very uniform illumination with precise adjustment of light incidence angle and illumination from 360 degrees azimuth. Lithography is one such application. It may also be useful as a fully adjustable illumination system for darkfield illumination in microscopes.

The present disclosure can best be described by reference to FIG. 1, wherein a collimated beam is formed by placing the light source 1 at the focal point of a lens 2 with focal length $f_2$. A mask 3 is used to block the center portion of the beam. The purpose of this mask is to prevent light from scattering from the center portion of axicon lens that is difficult to manufacture precisely.

A lens 4 of focal length $f_4$, focuses the light to a point in an image plane 8. A stationary axicon lens 5 shifts the direction of the converging beam in a radial outward direction such that the inside edge 7 is projected parallel to the optical axis of the system. This condition insures that shadow of the mask 3 on the adjustment axicon 6 does not vary with its position $x_6$. The converging beam is shifted further outward by the adjustment axicon 6 which can be translated along the optical axis between the stationary axicon 5 and the image plane 8.

The converging beam is focused on the image plane 8 where it creates an annular image. The radius of the annulus $r_8$ minimized when the adjustment axicon 6 is at its closest position to the image plane. At this location the annulus radius $r_8$ is nearly the radius of the blocking mask (neglecting the limiting effects of placing lenses at zero distance from each other). Moving the adjustment axicon 6 a further distance $x_6$ from the image plane 8 creates a linear change in the radius of the projected annulus. The axicon 6 can be mounted on a motorized stage 15 to allow software control of its position $x_6$. The following formula applies:

$$r_8 = r_3 + x_6 * \tan(\theta_6) + c$$

Where:
$r_8$=annulus radius
$r_3$=blocking mask radius
$x_6$=adjustment axicon distance from image plane 8
$\theta f_6$=deflection angle of adjustment axicon.
c=a constant correction term accounting for lens spacing Light from the illuminated ring in the image plane 8 is collimated by the illumination field lens 20 and centered on the pupil plane 100. If the various optical elements are chosen appropriately (as illustrated in FIG. 1) the center line of the converging beam 10 is parallel to the optical axis (Telecentric condition). This condition is unaffected by moving the adjustment axicon along the optic axis. In this arrangement the illumination area in the pupil plane 21 remains constant regardless of the illumination inclination angle. The pupil plane inclination angle $\theta_{100}$ of the illumination is determined by the annulus radius $r_8$ and by the focal length of the illumination field lens $f_{20}$ according to this formula:

$$\theta_{100} = \tan^{-1}(r_8/f_{20})$$

For small angles the following formula applies:

$$\theta_{100} = r_8/f_{20} \text{ [rad]} = 180/\pi * r_8/f_{20} \text{ [deg]}$$

The illuminated diameter $d_{100}$ is shown on the diagram. If necessary an iris or other blocking mask can be placed in the pupil plane 100 to reduce the size of the illuminated area.

To create uniform illumination at the pupil plane 100 a diffuser 12 is placed at the image plane 8. The focused light incident on diffuser 12 is scattered to fill pupil plane 100 with good uniformity. This diffuser is essential since without it an intense spot is created at the center of pupil plane 100. Ideally the surface of the diffuser should be moving rapidly to insure that any resultant speckle is averaged out of recorded measurements. This is accomplished with a spinning diffuser. Ideally the diffusing surface should be a holographic coating designed for a specific angular dispersion to issue the forward scattering is maximized and that most of the light is projected with uniform intensity onto desired region of the pupil. Other, non-static diffusers can be used with the restriction that the diffusing surface must be thin to avoid blurring the annular illumination pattern.

A microscope image plane 900 is typically an accessible location outside the body of the microscope. By placing pupil plane 100 of the illumination system at the microscope image plane 900, the illuminated area is relayed from the microscope image plane 900 to the objective focal plane 915 by the microscope tube lens 905, a beam-splitter 908 and the objective 910. In a similar way, the annular illumination pattern is relayed from the image plane 8 to the back pupil plane of the objective 909 by the illumination field lens 20, the microscope tube lens 905 and the beam-splitter 908. The size of the annular illumination pattern is rescaled by the ratio of the focal lengths:

$$r_{909} = r_8 * f_{905}/f_{20}$$

The incidence angle of the illumination $\Theta_{915}$ at the objective focal plane can be calculated by the following:

$$\begin{aligned}\Theta_{915} &= \tan^{-1}(r_{909}/f_{910b}) \\ &= \tan^{-1}((r_8 * f_{905})/(f_{20} * f_{910b})) \\ &= \tan^{-1}(((r_3 + x_6 * \tan(\theta_6) + c) * f_{905})/(f_{20} * f_{910b}))\end{aligned}$$

Thus the incidence angle of the illumination $\Theta_{915}$ is fully adjustable by varying the position $x_6$ of the adjustment axicon. The adjustment is most likely non-linear due to the high numerical aperture objectives used in microscopy applications.

The objective focal length on the focal plane side $f_{910b}$ may be different than the objective focal length on the pupil side $f_{910a}$ since the objective focal plane is usually contained within immersion media and the objective pupil is generally in air. Immersion media generally has an optical index of greater than 1.4.

$$f_{910b} = f_{910a}/\text{Immersion media optical index}$$

The resultant fluorescence 918 from the specimen is transmitted through the beamsplitter 908 and is viewed by an eyepiece or a camera located at position 920. Excitation and emission filters are not shown.

Variations

The order of the stationary optical elements 2,3,4,5 is not critical. The purpose of these optical elements is to create a converging beam of a particular size from a point source. Positive lenses 2 and 4 could be replaced by a single lens. The stationary axicon 5 could be integrated into a surface of a positive spherical lens. The design limiting factors are optical aberrations, color correction and space considerations.

If the required range of illumination angles is small it may not be necessary to include a stationary axicon 5. The shadow of the mask 3 would converge along with the converging beam. In this configuration the mask will be somewhat larger than necessary since it must block out the imprecise surface at the center of the adjustment axicon over the full range of adjustment. Minimizing the masked area is important since the center of the beam is generally the most intense. Depending on the range of adjustment required this might be acceptable.

It may be necessary to couple a laser to the illumination system without the use of an optical fiber, (i.e. ultraviolet lasers). In these cases a beam expander could be made to create a collimated beam which would then be converged by lens 4 or an integrated beam expander could be made that includes the function of the converging lens 4.

Image and Pupil Planes

In the present optical system, the stationary elements and adjustable axicon 6 create an image of an annulus at image plane 8. Diffuser 12 is placed with its diffusing surface in this plane. Adjustment of adjustable axicon 6 varies the radius of the annulus. In order to create the necessary illumination conditions for TIRF imaging the annular image is relayed to the back pupil of an objective. In the case of an add-on design this is accomplished by telescope comprised of a field lens 20 and the microscope tube lens 905. The field lens 20 creates a stationary pupil plane 100. To couple the illumination system (parts 1-100) to the microscope (parts 900-920) the illumination system pupil plane 100 is placed at the image plane 900 of the microscope. If a pupil plane of the microscope exists in an accessible location (i.e. outside the microscope chassis) it may be possible to couple the illumination to the microscope without the field lens 20. In this case the illumination system is placed such that the diffusing surface of the diffuser 12 is positioned coincident with that pupil plane.

If the back pupil plane of the objective lens is accessible (i.e. outside the body of the objective) it may be possible to couple the illumination to the objective without additional optics. In this case the illumination system is placed such that the diffusing surface of the diffuser 12 is positioned coincident with the back pupil plane 909 of the objective lens. This coupling is most applicable to fully integrating the illumination optics into an imaging system.

An integrating rod can be used to couple light from the illumination pupil plane 100 to the microscope image plane 900. This will slightly improve the uniformity of the light intensity without altering the lights incidence angle with respect to the optical axis of the system.

A field stop (aperture) can be placed at the microscope image plane 900 to restrict the area of the illumination. This can be any shape, and can be matched to the shape and orientation of the image recording device (usually rectangular).

What is claimed is:

1. An illumination system for shaping a light beam, said system comprising:
    a light source for emitting said light beam;
    an optical assembly that receives said light beam and thereafter converges said light beam to form an annular image;
    an adjustable axicon lens for adjusting said annular image and focusing said annular image on an image plane;
    a diffuser disposed with its diffusing surface in said image plane; and
    an illumination field lens disposed such that said system provides illumination through an objective at a precise inclination angle and with uniform intensity across an illuminated field.

2. The system according to claim 1, wherein said light source is at least one selected from the group consisting of: an optical fiber and a laser.

3. The system according to claim 2, wherein said laser is at least one selected from the group consisting of: an ultraviolet laser, a visible laser, an infrared laser, and a pulsed laser.

4. The system according to claim 1, wherein said optical assembly comprises at least one optical element selected from the group consisting of: a lens, a mask and a stationary axicon lens.

5. The system according to claim 4, wherein said optical assembly comprises a first lens, a stationary axicon lens, a mask and a second lens.

6. The system according to claim 5, wherein said first lens is disposed between said light source and said stationary axicon lens, said mask is disposed between said stationary axicon lens and said second lens, and said second lens is disposed between said mask and said adjustable axicon lens.

7. The system according to claim 1, wherein the position of said adjustable axicon lens is adjustable with respect to the position of said image plane.

8. The system according to claim 1, wherein said adjustable axicon lens is adjustable either manually or automatically.

9. The system according to claim 1, wherein said optical assembly converges said light beam from said light source, thereby forming said annular image, and said adjustable axicon lens controls a radius of said annular image; wherein said annular image is focused on said image plane.

10. The system according to claim 1, further comprising an illumination field lens and a pupil plane, wherein said illumination field lens is disposed between said diffuser and said pupil plane.

11. The system according to claim 10, wherein said illumination field lens collimates light from said image plane and centers said collimated light on said pupil plane.

12. The system of claim 1, wherein said optical assembly comprises a mask that is shaped and disposed to prevent light from scattering a center portion of said adjustable axicon lens.

13. The system of claim 1, wherein said diffuser spreads out and temporally varies the illumination in said image plane so as to eliminate speckle and to provide a uniform illumination field.

14. The system of claim 13, wherein said diffuser is movable.

15. A method for shaping a light beam comprising:
    emitting said light beam from a light source;
    passing said light beam through an optical assembly wherein said light beam is converged to form an annular image;
    adjusting the radius of said annular image;
    focusing said annular image on an image plane;
    diffusing the light of said annular image from said image plane; and
    providing illumination through an objective at a precise inclination angle and with uniform intensity across an illuminated field.

16. The method according to claim 15, wherein said light source is at least one selected from the group consisting of: an optical fiber and a laser.

17. The method according to claim 16, wherein said laser is at least one selected from the group consisting of: an ultraviolet laser, a visible laser, an infrared laser, and a pulsed laser.

18. The method according to claim 15, wherein said optical assembly comprises at least one optical element selected from the group consisting of: a lens, a mask and a stationary axicon lens.

19. The method according to claim 18, wherein said optical assembly comprises a first lens, a stationary axicon lens, a mask and a second lens.

20. The method according to claim 19, wherein said radius of said annular image is adjusted by an adjustable axicon lens and wherein said first lens is disposed between said light source and said stationary axicon lens, said mask is disposed between said stationary axicon lens and said second lens, and said second lens is disposed between said mask and said adjustable axicon lens.

21. The method according to claim 20, wherein the position of said adjustable axicon lens is adjustable with respect to said image plane.

22. The method according to claim 20, wherein said adjustable axicon lens is adjustable either manually or automatically.

23. The method according to claim 15, further comprising collimating light from said image plane and centering said collimated light on a pupil plane.

24. The method of claim 15, wherein said radius of said annular image is adjusted by an adjustable axicon lens, and wherein said optical assembly comprises a mask that is shaped and disposed to prevent light from scattering a center portion of adjustable axicon lens.

25. The method of claim 15, wherein said diffusing step spreads out and temporally varies the illumination in said image plane so as to eliminate speckle and to provide a uniform illumination held.

26. The method of claim 25, wherein said diffusing step uses a movable diffuser.

27. A microscope assembly comprising:
a light microscope; and
an illumination system for shaping a light beam, said system comprising:
a light source for emitting said light beam;
an optical assembly that receives said light beam and thereafter converges said light beam to form an annular image;
an adjustable axicon lens for adjusting said annular image and focusing said annular image on an image plane; and
and a diffuser disposed with its diffusing surface in said image plane.

* * * * *